United States Patent [19]

Nagatsuka et al.

[11] Patent Number: 5,283,736
[45] Date of Patent: Feb. 1, 1994

[54] RADIOGRAPHIC IMAGE PROCESSING APPARATUS

[75] Inventors: Sumiya Nagatsuka; Hisanori Tsuchino, both of Hino, Japan

[73] Assignee: Konica Corporation, Tokyo, Japan

[21] Appl. No.: 798,519

[22] Filed: Nov. 26, 1991

[30] Foreign Application Priority Data

Nov. 29, 1990 [JP] Japan ................................. 2-325605

[51] Int. Cl.$^5$ .............................................. G06F 15/00
[52] U.S. Cl. ............................................... 364/413.13
[58] Field of Search ................. 364/413.13, 413.22; 382/2, 6, 22, 48, 50

[56] References Cited

U.S. PATENT DOCUMENTS

| | | | |
|---|---|---|---|
| 4,602,156 | 7/1986 | Asai et al. | 250/327.2 |
| 4,891,757 | 1/1990 | Shroy, Jr. et al. | 364/413.13 |
| 4,970,393 | 11/1990 | Funahashi | 250/327.2 |
| 5,003,616 | 3/1991 | Orita et al. | 282/50 |
| 5,029,226 | 7/1991 | Klein et al. | 282/50 |
| 5,151,947 | 9/1992 | Nagatsuka et al. | 382/6 |

FOREIGN PATENT DOCUMENTS

| | | | |
|---|---|---|---|
| 0150834 | 8/1985 | European Pat. Off. | G01T 1/29 |
| 0154131 | 1/1988 | European Pat. Off. | G01T 1/29 |

*Primary Examiner*—Roy N. Envall, Jr.
*Assistant Examiner*—Ari M. Bai
*Attorney, Agent, or Firm*—Frishauf, Holtz, Goodman & Woodward

[57] ABSTRACT

The invention provides an apparatus for processing digital image data of pixels which are obtained by radiographing an image area including a subject so as to generate image signals and by converting the image signals into digital image data, each of the digital image data representing a density level corresponding to an amount of radioactive ray transmitted through each portion of the image area. The apparatus comprises a circuit for analyzing the digital image data of pixels; and a circuit for determining a desired portion of said image area on the basis of the analyzing result and for further determining an image processing condition for the image area on the basis of digital image data of the desired portion.

19 Claims, 9 Drawing Sheets

EFFECTIVE IMAGE AREA

NARROWED RADIATION FIELD

RADIOGRAPHIC IMAGE PROCESSING APPARATUS

BACKGROUND OF THE INVENTION

The present invention relates to an image processing apparatus for a radiographic image which is photographed using radioactive rays such as X-rays or the like.

Furthermore, the present invention relates to a method determining an image area used when a radiographic image which is photographed using radioactive rays such as X-rays or the like is image-processed.

When a radiographed image is digitalized and relayed through a network, the image can be processed, transmitted, stored, and retrieved, so that a more easy medical diagnosis can be achieved. However, a radiographed image having high diagnostic capacity is required. In order to improve diagnostic appropriateness, it is necessary to conduct image-processing on the radiographed image. Among various kinds of image processing, gradation processing is achieved with only a simple apparatus and has superior effects. An example of a conventional image processing techniques of gradation processing will be described as follows.

When gradation processing is conducted on a radiographed image, a condition of the gradation processing is first determined from the statistical characteristics of data such as the maximum value, the minimum value, or a histogram of data of the entire image, and then the entire image is subjected to gradation processing.

However, the statistical characteristic of image data differs on each image data depending on factors such as a patient's FIGURE, or photographing conditions such as, for example, a radiation exposure amount, a photographing time, or a voltage on a photoelectric converter. Therefore, there arises a problem in that optimum image processing data can not be secured when image processing is conducted by determining the signal value of a predetermined portion of the image data according, for example, to the histogram.

SUMMARY OF THE INVENTION

In view of the foregoing, an object of the present invention is to provide an image processing apparatus in which optimum image processing data can be obtained for each image data even when photographing conditions differ.

According to the present invention, there is provided an image processing apparatus capable of image-processing of a radiographed image formed corresponding to an amount of radioactive rays transmitted through each portion of a subject. The present invention comprises an image area determination means by which whole data of a radiographed image can be analyzed and a desired image area is determined, an image processing condition determination means by which a image processing condition is determined according to an signal value in the desired image area, and a image processing means by which the aforementioned radiographed image is image-processed according to the determined image processing condition.

In the manner described above, the radiographed image is image-processed after a desired image area is determined by the analyzation of the radiographed image and an image processing condition is determined according to a signal value in the desired image area.

Another object of the present invention is to provide an image area determination method by which optimum image processing data can be obtained for each image data even when photographing conditions are different.

According to the present invention, a desired image area is determined from the plurality of image areas after a radiographed image, which is formed corresponding to an amount of radioactive rays which are transmitted through each portion of a subject, has been divided into a plurality of image areas.

In the manner described above, in the present invention, as a radiographed image has been divided into a plurality of image areas, a desired image area is determined from those image areas, and optimum image processing can be conducted.

DETAILED DESCRIPTION OF THE PREFERRED EMBODIMENT

Referring to drawings, an embodiment of the present invention will be described as follows. In the explanation of the embodiment, a radioactive ray is exemplified by an X-ray.

Figure 1:
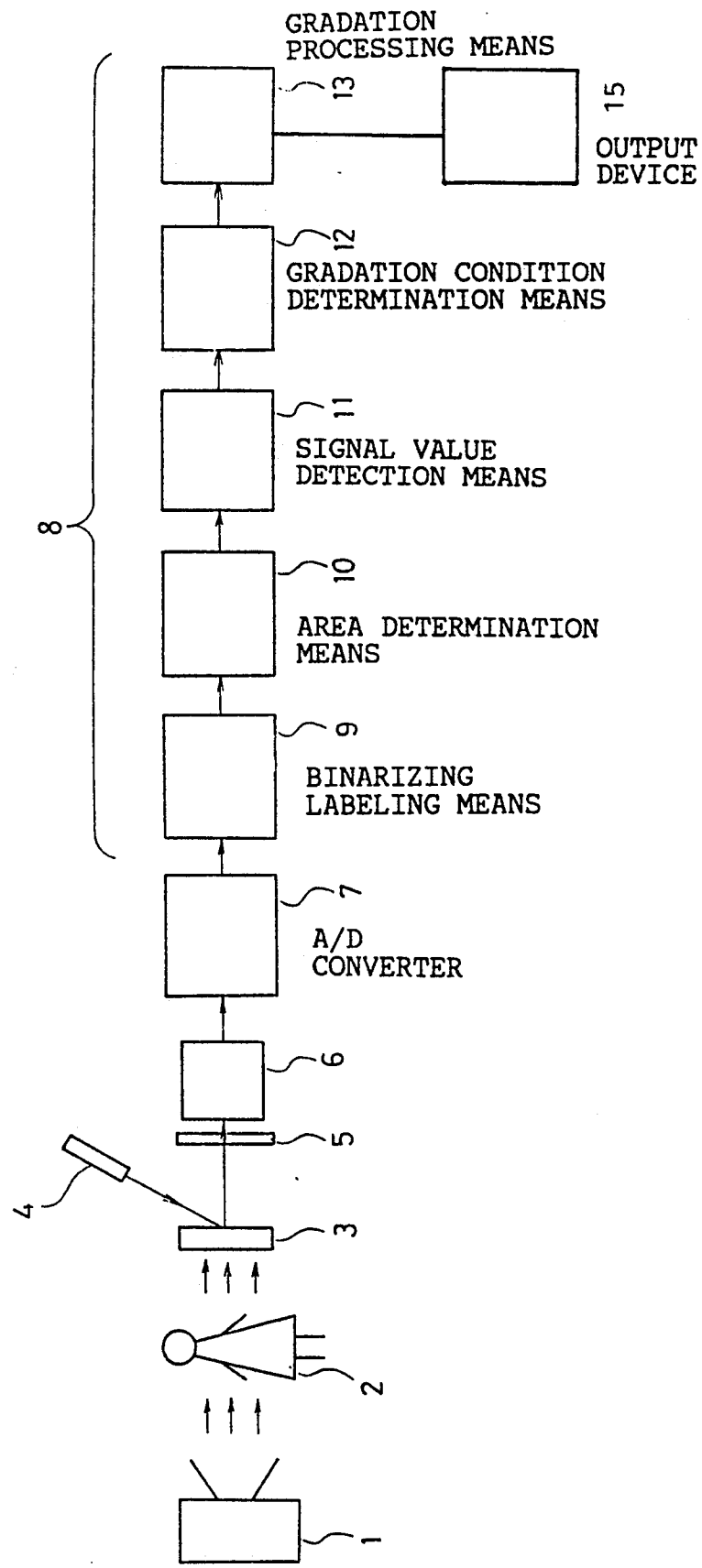
FIG. 1 shows an embodiment of the present invention.

In FIG. 1, an X-ray emitted from an X-ray irradiation unit 1 which is composed of an X-ray tube or the like, is transmitted through a subject and irradiated on a radiation image conversion panel 3. The aforementioned radiation image conversion panel 3 has thereon a stimulation fluorescent substance layer, and when excitation light such as an X-ray, electron beam, or ultraviolet ray is irradiated on the fluorescent substance, a portion of excitation light energy is accumulated in the fluorescent substance corresponding to the irradiated amount.

Stimulation excitation light such as visible light, infrared ray, or the like from a stimulation excitation light source 4 is irradiated through scanning on the aforementioned radiation image conversion panel 3. Responding to this irradiation, the radiation image conversion panel 3 emits stimulation fluorescent light proportional to the accumulated energy. This emitted light is inputted into a photoelectric converter 6 through a filter 5, and the photoelectric converter 6 outputs a current signal proportional to intensity of emission to an analog/digital (A/D) conversion unit.

The filter 5 is a separation filter which separates a stimulation fluorescent light from a light beam emitted from the stimulation excitation light source 4, and makes only the stimulation fluorescent light enter into the photoelectric converter 6.

Figure 2:
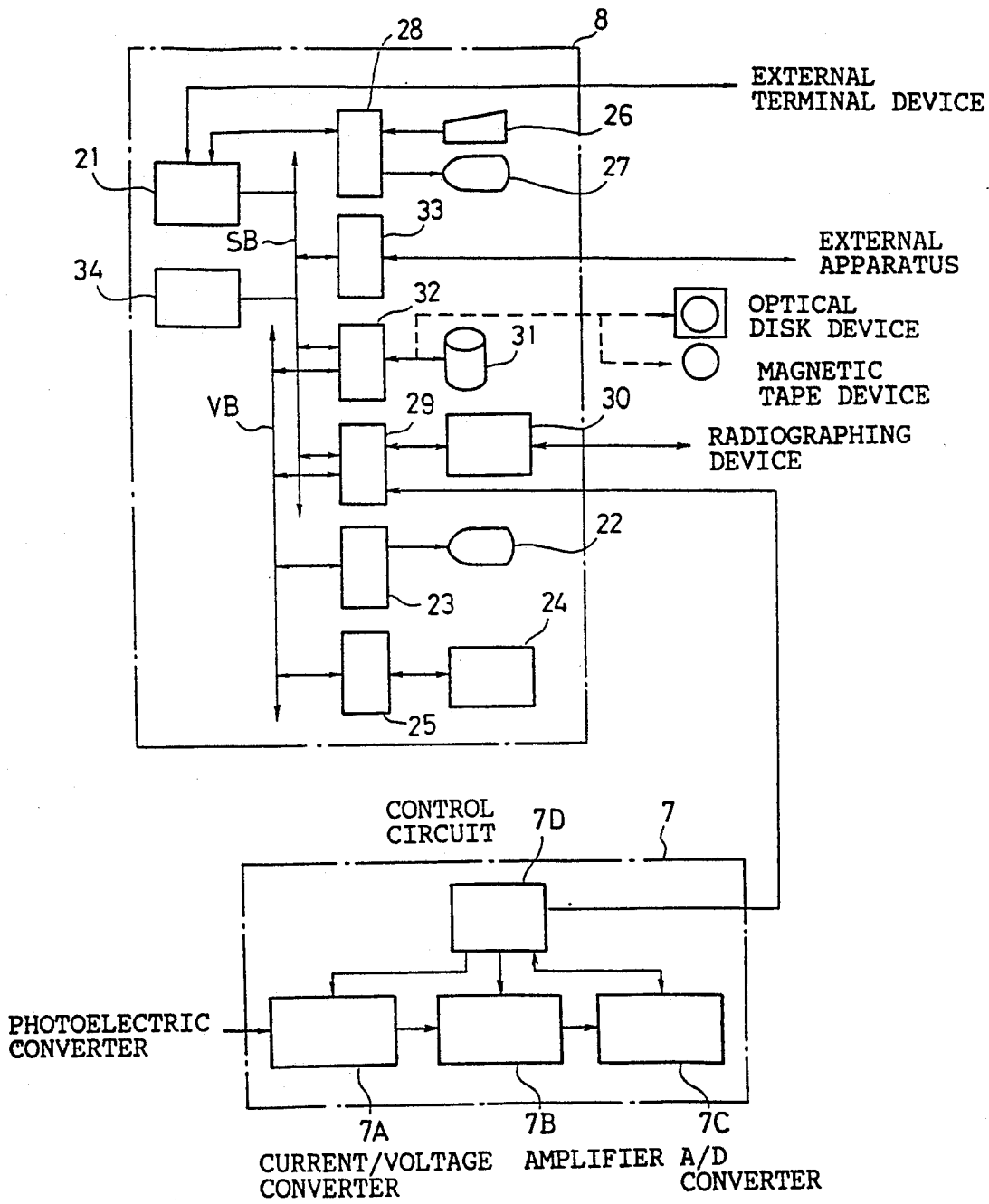
FIG. 2 shows a composition of the hardware of the embodiment in FIG. 1.

The A/D converter 7 converts the inputted current signal into a digital image data to output the data to an image processing apparatus 8. As shown in FIG. 2, a hardware of the A/D converter 7 is specifically composed as follows: a current/voltage converter 7A which converts the output current from the photoelectric converter 6 into a voltage signal, is provided so that the output voltage from the current/voltage converter 7A is inputted into an A/D converter 7C through an amplifier 7B. In this case, a logarithmic amplifier may be used as the amplifier 7B. The A/D converter 7C converts an analog voltage into a digital voltage (a digital image data) and outputs it to a control circuit 7D. The control circuit 7D adjusts gains of the current/voltage converter 7A and amplifier 7B, and adjusts an input dynamic range of the A/D converter. In addition, the control circuit 7D totally adjusts the reading gains of the radiographed image information and transmits the image data to the image processing apparatus 8 on a predetermined timing basis.

The image processing apparatus 8 has the aforementioned digital image data stored in a memory, and conducts input/output control of data for a CRT display or a film output, and further conducts setting of photographing conditions for the subject, or conducts successively various image processing (for example, space-frequency processing, enlargement, reduction, movement, statistic processing and the like) including the gradation processing of the image data.

In this case, the radiation image conversion panel 3 is structured in a manner that: the radiation conversion panel 3 can be repeatedly used for photographing, reading and erasing; and a radiation exposure range in which data can be recorded is extremely wide, so that any difference in photographing conditions can be corrected and restored by image processing. Furthermore, communication processing by which digital image data is transmitted to a host computer, and reproducing of the image as a hard copy by sending the digital image data to an image output device 15 to record it in a film and developing it, can be conducted in the image processing apparatus 8.

As shown in FIG. 1, the image processing apparatus 8 is provided with: a binarizing/labeling means 9 which will be described later; an image area determination means 10; a signal value detection means 11; a gradation processing determination means 12; and a gradation processing means 13.

A specific composition of hardware of the image processing apparatus 8 is shown in FIG. 2. As shown in FIG. 2, a central processing unit (hereinafter called CPU) 21 is provided in the apparatus, and an image monitor 22 is connected with the CPU 21 through a display control unit 23 and an image bus VB.

The CPU 21 is connected also with a frame memory 24 in which the image processing data is stored, through a frame memory control unit 25 and the image bus VB.

Further, a keyboard 26 which inputs the subject's identification information (name, sex, date of birth, or the like), and a display unit 27 which displays the inputted information are provided in the apparatus. The key board 26 and the display unit 27 are connected with the aforementioned CPU 21 through an interface 28.

A timing control unit 29 is provided for outputting timing control signals. The timing control unit 29 outputs the timing control signal to the drive circuit of the aforementioned X-ray irradiation unit 1 through an adapter 30, and outputs the signal to the aforementioned control circuit 7D. A magnetic memory 31 storing the image data is provided in the apparatus. The image data which is image-processed is stored in the magnetic memory 31 according to the signal from a magnetic disc control unit 32. In this case, as shown by a broken line in FIG. 2, the image data may be stored through an optical disc unit or a magnetic tape unit which is provided outside the apparatus.

The numeral 34 represents a memory which stores a control program or the like. The numeral 33 represents an I/O interface provided for outside devices by which the image processing apparatus 8 can be connected.

In this case, the CPU 21 composes the binarizing/labeling means 9, the image area determination means 10, the signal value detection means 11, the gradation processing determination means 12, and the gradation processing means 13.

Figure 3:
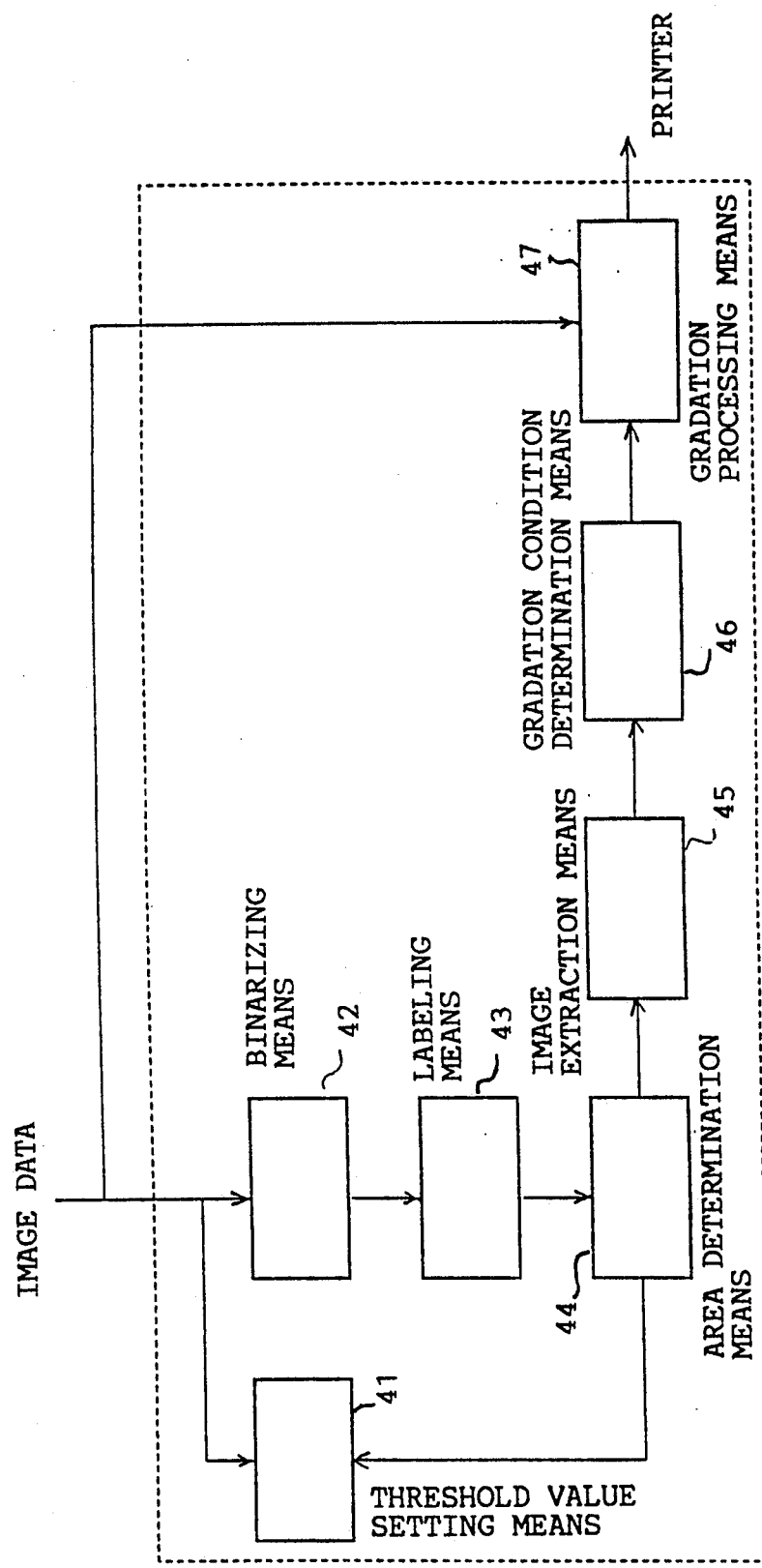
FIG. 3 is a block diagram showing a portion of an image processing apparatus for determining a desirable image area.

Referring to FIG. 3, functions of the CPU 21 will be described in detail as follows.

That is, original radiographic image data read out from the stimulation fluorescent substance layer provided on the radiation image conversion panel 3 is binarized by being compared with a predetermined threshold level in a binarizing unit 42, and given an identification code so that an image area can be determined in order to decide a gradation processing condition before gradation processing. For example, a pixel higher than the threshold value is given an identification code 1, and a pixel less than the threshold value is given an identification code 0. The threshold value used in the aforementioned binarizing is given by a threshold value determination unit 41, and an initial value of the threshold value is set by the threshold value determination unit 41 according to each radiation image data.

In the aforementioned binarizing processing, when an exposure area of an X-ray is restricted, or there is specific information concerning the subject, processing is not conducted on the entire image and processing may be conducted on only an effective image area, however when there is not the aforementioned condition, processing is preferably conducted on the entire image.

In the labeling unit 43, the labeling processing is conducted by judging the continuity of the identification code corresponding to the image data which is coded by identification in the aforementioned binarizing unit. Specifically, when a plurality of pixels each having the identification code 1 adjoin each other continuously, the same label A is given to the whole pixels of a group of continuing pixels. When a plurality of pixels each having the identification code 1 adjoin each other continuously in the other portion, the other label B is given to the whole pixels of a group of continuing pixels. This operation is conducted for all groups of continuing pixels. Accordingly, the binarizing/labeling means is composed of the threshold value setting unit 41, binarizing unit 42, and labeling unit 43.

A plurality of pixels continuously adjoining each other, can take the following cases. One is a case where pixels adjoining a predetermined pixel in the directions of upper, lower, left and right sides have the same identification code, and the other is the case where pixels adjoining a predetermined pixel in the diagonally upper and lower directions have the same identification code, in addition to the aforementioned directions. When labeling processing is conducted, in addition to the aforementioned continuity of the identification codes, the number of continuing pixels may be added to the judgement standard, for example, the label may be given to only the pixel group in which the number of pixels not less than n (n is an integer not less than 1, preferably, $2 \leq n$) is continued. Labeling may be conducted on both identification codes, however, it may preferably be conducted on only one of the codes. Specifically, when the maximum value is searched, it is better that the labeling is conducted on only the pixels having the aforementioned identification code 1, and when the minimum value is searched, the labeling is conducted on only the pixels having the identification code 0.

Next, in the image area determination unit 44, a desired image area is determined from the labeled areas. Specifically, the necessary pixel group is selected from a plurality of labeled groups according to, for example, information regarding the pixel positions or signal level in the radiation image. The number of selected pixel groups may be one or more.

At this time, when the desired image area can not be searched, the threshold value is changed (for example it is reduced), in the aforementioned threshold value setting unit 41, and the operation is repeated again from the binarizing processing.

Therefore, an image area determination means is composed of the threshold value determination unit 41, the binarizing unit 42, the labeling unit 43 and the image area determination unit 44.

When the aforementioned desired image area is determined, an image data extraction unit 45 as a signal detection means processes statistically the image data in the image area, extracts the information which is necessary in a next gradation processing condition determination unit 46, and then outputs the aforementioned extracted information into the gradation processing condition determination unit 46. The gradation processing condition determination unit 46 as a gradation processing condition determination means determines the gradation processing condition according to the information from the aforementioned data extraction unit 45. Specifically, when the radiation image is reproduced in the aforementioned image output device 15, a gradation processing table is corrected according to the aforementioned information so that the image may have such density and gradation characteristics that the image can easily be read in a diagnosis. When the gradation condition is determined in the manner described above, a gradation processing unit 47 as a gradation processing means conducts gradation processing of the original radiation image data, and then outputs the image data into the image output device 15.

As image data used in the other portion excluding the gradation processing unit 47, all data (all pixels) read in the image reading device 14 are not necessary. The process for the gradation processing condition determination may be simplified by using the image data selected from the original image data, or the image data obtained from averaging the original image data.

Furthermore, the gradation processing condition is caused to be determined according to the image data obtained by "preliminary reading" as disclosed in Japanese Patent Publication Open to Public Inspection No. 67240/ 1983, and then the image data obtained by "regular reading" may be processed according to the processing condition determined as described above.

In the above example, the gradation processing is described as the image processing, however, it is needless to say that the present invention can be applied to image processing such as frequency processing.

Figure 4:
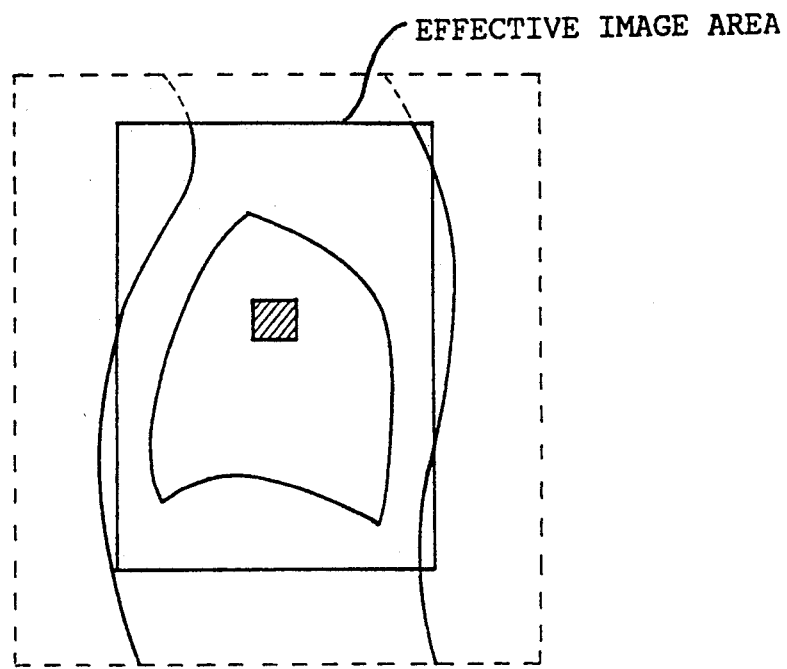
FIGS. 4, 5 and 6 are views which explain operations of the foregoing.

Next, the state of the desired image area determination or image processing according to the present invention whose detailed structure is shown in FIG. 3, will be explained more precisely taking the case of a side view of a human chest as the photographing subject. FIG. 4 shows a typical human side view, and the original human side view is composed of 2048 pixels in the lateral direction, and 2464 pixels in the longitudinal direction. Each pixel signal is A/D converted after passing through a logarithmic converter, and the number of gradation is 1024.

At first, photographing of a subject will be described as follows. When a photographing button (not shown in the drawings) is pressed, the timing control unit 29 drives the X-ray irradiation unit 1 through the X-ray adapter 30, thus the subject 2 is irradiated with X-rays in a predetermined amount. The X-rays are transmitted through the subject 2 and are inputted into the radiation conversion panel 3 wherein energy corresponding to the amount of X-ray transmitted through the subject are accumulated, and thus the latent image of the subject 2 is formed there.

When photographing is completed and stimulation excitation light is irradiated on the radiation image conversion panel 3 from the stimulation excitation light source 4, the radiation conversion panel 3 emits light in proportion to latent image energy. The light is photoelectrically converted into current signals in the photoelectric converter 6 so that the current signals are inputted into the A/D conversion unit 7. The output current is converted into digital image data through the current-/voltage converter 7A, the amplifier 7B, and the A/D converter 7C so that the digital image data is inputted into the control circuit 7D. The digital image data is transferred from the control circuit 7D, through the timing control unit 29, the image bus VB, and the frame memory control unit 25, to the frame memory 24 where it is stored. The CPU 21 reads the control program from the memory 34 through the system bus SB, and further, reads the radiographed image data from the frame memory 24 through the image bus VB and the frame memory control unit 25. Then, the CPU 21 conducts the following operations according to the control program.

Next, the aforementioned original human side image is subjected to culled-out processing into 1/16 in both longitudinal and lateral directions in order to reduce the number of pixels and thereby improve the following processing speed. Furthermore, for the same purpose, an effective image area is selected from the whole of the aforementioned human chest side view (a rectangular area surrounded by the broken line in FIG. 4). In the example, in view of the following characteristics of the human chest side view, the effective image area is selected in a manner in which: left and right portions and upper and lower portions of the image are cut off and the area surrounded by the real line in FIG. 4 is selected.

① In left and right portions of the image, there is a non-subject portion (a low density portion).

② In the lower portion of the image, there is an unnecessary upper portion of the abdominal region.

③ In the upper portion of the image, there is an unnecessary image of the neck.

Except the method in which characteristics common to the image are used as the foregoing, the effective image area may be set individually at each image. Especially, the binarizing processing of the low density portion results in loss of time, and therefore, the effective image area is preferably set so that the low density portion can be cut off as much as possible.

Figure 6:
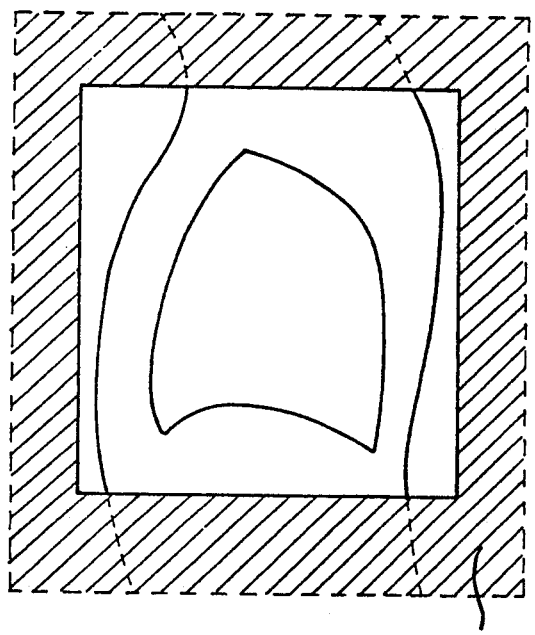

In the case of the image which is photographed by narrowing the radiation field of X-rays (refer to FIG. 6), the effective area may be determined in a manner in which: the image data is analyzed; and the radiation field is detected according to the signal from the X-ray radiation apparatus 1.

Processing after binarizing processing is conducted on the culled-out image data in the effective image area except gradation processing in the gradation processing unit. In this example, the number of pixels in the effective image area is 88 in the lateral direction and 118 in the longitudinal direction.

Next, an initial value of the threshold value which is used in the binarizing processing of the image data is set in the threshold value setting unit 41. The first object of the present example is to detect the maximum image data (the maximum signal value) in the lung field as a subject field, and in order to accomplish the object, it is necessary to change the threshold value for binarizing gradually from the large value to the direction of the optimum threshold value.

The signal value is set to initial value P1 by adding 100 to the maximum signal value (M1) of the pixels of $8 \times 8$ in an almost central portion in the aforementioned effective image area (a slanting line portion in FIG. 4). When the threshold value is reduced gradually, the initial value needs to be larger than the aforementioned optimum threshold value, and therefore the maximum value of the signal value which can be processed as data may be set as the initial value, however, in the setting described above, the difference between the initial value and the optimum threshold value becomes large, resulting in long processing time.

Figure 7:
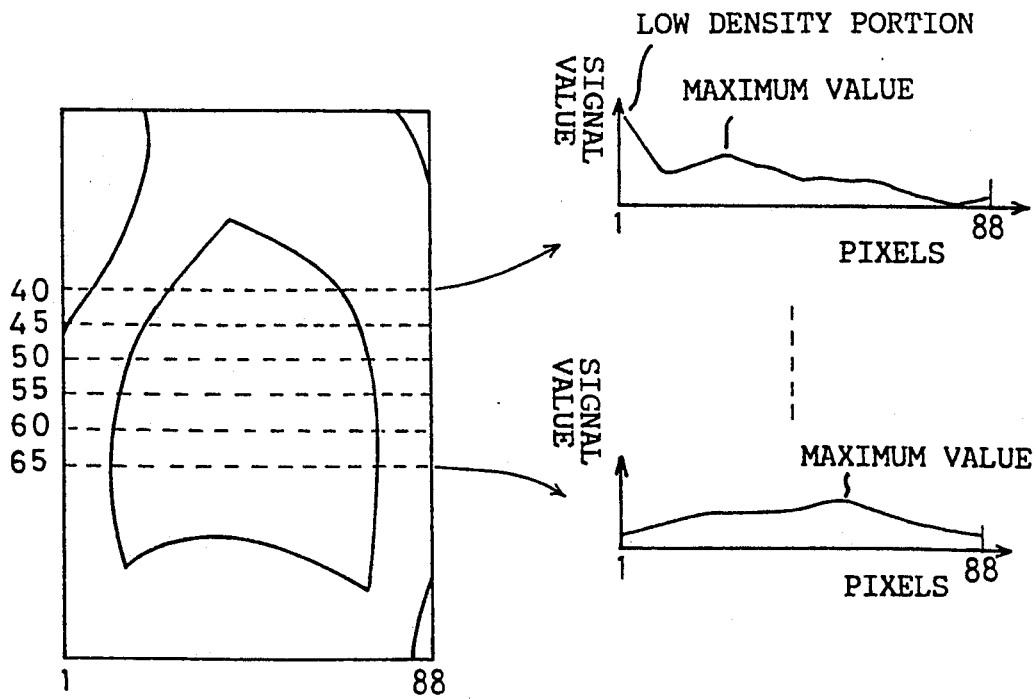
FIG. 7 is an illustration to explain a method of setting an initial value.
Figure 8:
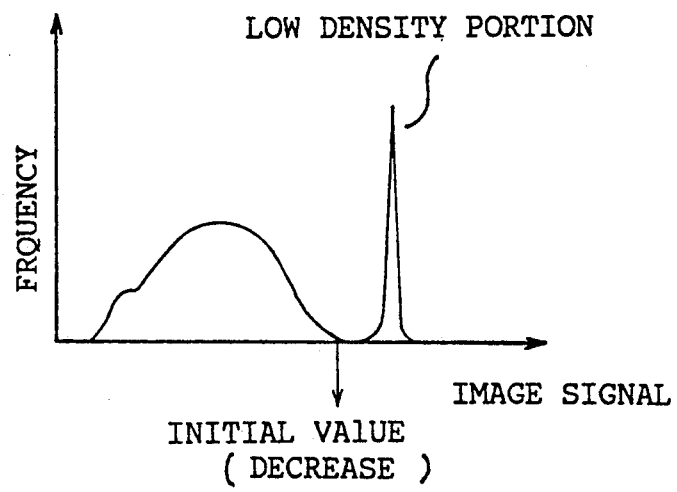
FIG. 8 is a histogram used for determining an initial value.

There are other methods of the initial value setting as follows: the method in which the maximum value of the image data except the low density portion of several lines (for example, 40, 45, 50, . . . , 65 lines) in the almost central portion in the effective image area as shown in FIG. 7 is sought to be set as the initial value; the method in which a histogram in the effective image area is sought as shown in FIG. 8, and the maximum value except the low density portion of the histogram is set as the initial value; and the method in which the signal value of a predetermined percentage of the accumulative histogram is set as the initial value.

On the other hand, when the threshold value is increased gradually from the smaller value, the value smaller than the minimum threshold value needs to be set as the initial value. Therefore, the minimum value in the image data range may be set as the initial value. However, due to the above, it is desirable to set the initial value according to the characteristics of the individual image.

In the binarizing unit 42, the image data corresponding to each pixel in the effective image area is compared with the threshold value, and the pixel having a higher value than the threshold value is discriminated from the pixel having a lower value than the threshold value. For example, the identification code 1 is given to the pixel higher than the threshold value, and the identification code 0 is given to the pixel lower than the threshold value, and thereby the image data in the effective image area is made to be a binarized image coded by "1" or "0".

Due to the foregoing, each pixel is allotted "1" or "0" for binarizing, and after that, labeling of the area is conducted according to the code of each pixel, and thereby the area is divided into a plurality of areas as sets of the same identification code. Specifically, in the system in which the threshold value is decreased gradually in order to determine the desired image area as in the case of this example, the area composed of pixel groups having image data higher than the threshold value is an area which should be marked. In this case, relating to only the pixel having the identification code 1, when three or more pixels adjoin each other continuously, all pixels are labeled by, for example, the same label A. The judgement of the continuity of the pixels includes the case where the pixels are diagonally arranged in addition to the case where the pixels are arranged in upper and lower, and left and right directions. In the same manner, a plurality of pixel groups in which the image data has a value higher than the threshold value are labeled respectively by different labels.

In the method in which the threshold value is increased gradually to determine the desired image area, the area composed of pixel groups having image data not more than the threshold value is the area which should be marked. Therefore, relating to only the pixels having the identification code 0, when two or more pixels adjoin each other, the whole pixels are labeled by the same label.

Then, an image area judgement unit 44 judges whether the desired area exists in a plurality of image areas determined as described above. That is, the image area judgement unit 44 judges whether the image area is the desired image area according to the relative positional relation of the aforementioned plurality of image areas in the effective image area, and when there are at least one or more image areas, the process advances to the next image data extraction unit. When there is not the desired image area, the threshold value is decreased, and processing from binarizing is repeated. The decreased width of the threshold value is preferably about 1 to 50 steps.

As the judgement method as to whether the image area is the desired image area or not, the judgement method may be a method in which the statistical characteristic of the data in the image area is utilized, except the aforementioned method by the relative positional relation. For example, there is a method in which the maximum value of the image data contained in the image area is compared with the maximum value of the image data in the effective image area, and the difference is judged as to whether it is in a predetermined area or not. Of course, a plurality of judgement methods may be used at the same time to increase the accuracy, and this method is more preferable.

Figure 5:
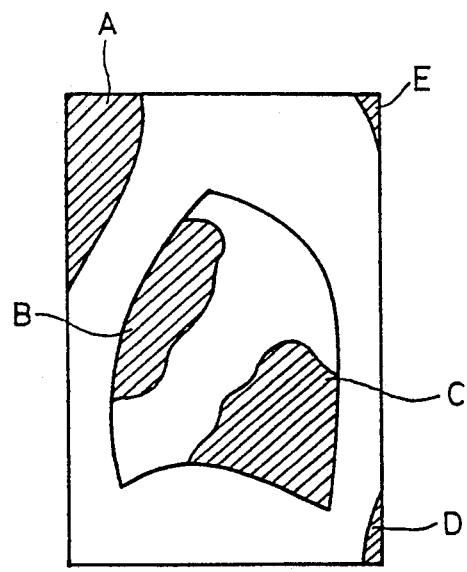

In this example, when 5 areas of A, B, C, D, and E are labeled as shown in FIG. 5, the areas of A, D, and E which contact with any one of the upper, lower, left or right end portions of the aforementioned labeled areas, are rejected, and the areas of B and C are determined as desired image areas. That is, the reasons are as follows: the lung field as the subject field is in the central portion of the image; therefore, the areas to be labeled do not come into contact with the aforementioned upper, lower, left or right end portions; and on the contrary, the low density portions always come into contact with the upper, lower, left or right end portions.

Next, in an image data extraction unit 45, the image data in the aforementioned B and C areas is statistically processed, and then an average value of the image data in the desired area is extracted. The average value expresses almost maximum image data (the maximum signal value) S1 in the lung field as the subject field. The maximum value, minimum value, intermediate value, histogram processing and the like, except the average value, may be used as the aforementioned statistical processing.

Figure 9:
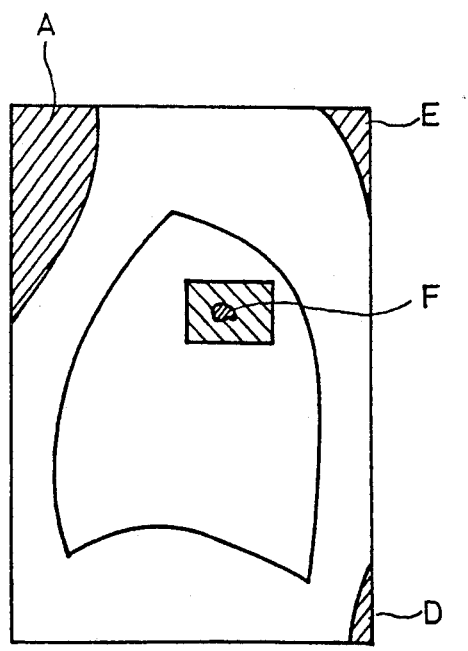
FIG. 9 is an illustration to explain an example to set a rectangular area around the desired image area.

In this example, the almost maximum image data of the lung field is extracted by using only the image data in the aforementioned desired image area. However, it is also possible that an area broader than the desired image data is determined around the desired image area as a center, or from the image area as an end point, and then the almost maximum image data of the aforementioned lung field is found according to the image data in the area. FIG. 9 shows the case where a rectangular area is set around the desired image area F. This method is effective in the case where the aforementioned image area is relatively small, and especially, extraordinary data due to noises or the like exists in the image data.

Figure 10:
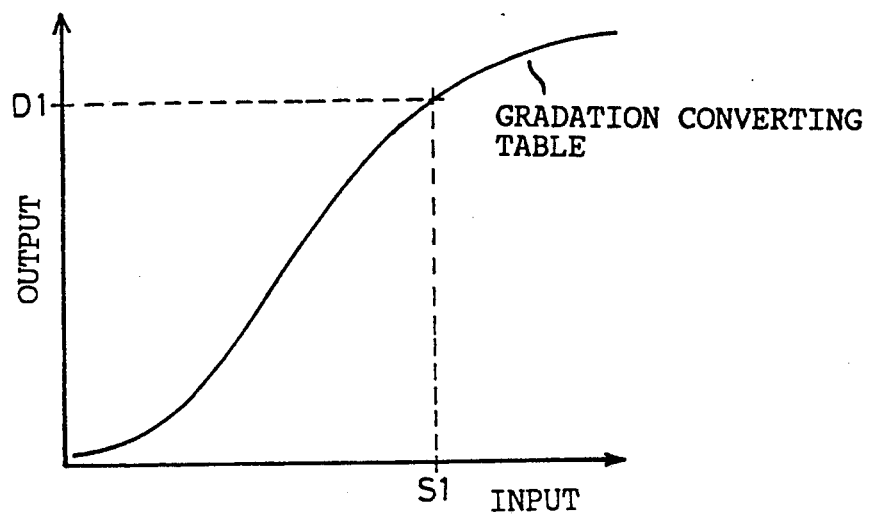
FIG. 10 is a diagram indicating a gradation conversion table.

When the almost maximum image data in the lung field is extracted from each image, a gradation processing condition determination unit 46 determines the gradation processing condition according to the maximum image data in the aforementioned lung field. The gradation processing condition is determined as follows: for example, as shown in FIG. 10, a gradation conversion table is set in a manner in which the pixel corresponding to the maximum image data S1 in the lung field has a density D1 which can be easily read in a diagnosis (for example, a penetration density 2.0). A gradation processing unit 47 gradation-processes the entire original radiation image data according to the gradation processing condition determined in the manner described above.

As described above, the almost maximum image data (the maximum signal value) in the lung field as the subject field can be detected for each image without being influenced by photographing conditions or physical constitution, and then, an image processing condition for finishing the subject field so as to be easily read can be accurately set by using the almost maximum image data in the aforementioned lung field, and appropriate image processing can be stably conducted.

Figure 11:
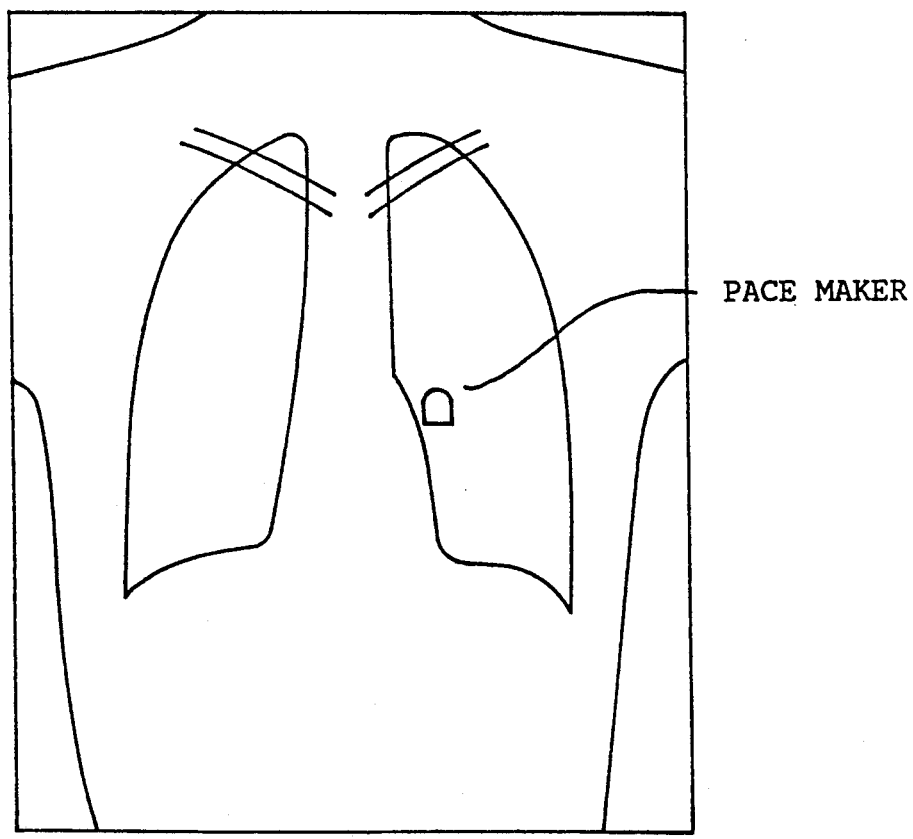
FIGS. 11, 12, and 13 are illustrations showing a part of human body.

The operation of FIG. 3 will be explained in detail by taking the front image of a human chest as a subject for example. FIG. 11 shows the human front image typically, and the number of pixels and the number of gradations of the original front image of a human body are the same as the case of the side image of the human body.

The image data of the aforementioned original front image of the human body is filter processed by a filter having the size of 60×60 pixels to cut a high frequency component in order to reduce failure in binarizing processing caused by noise, and pixels are culled out to 1/16 in both the longitudinal and lateral directions in order to reduce the number of pixels so that the processing speed in the following processes can be improved. The filter processing may be conducted after the cullout processing, and in this case, the processing speed is preferably improved.

Processing after the binarizing processing is conducted using the culled-out image data apart from gradation processing in the gradation processing unit. In this case, the effective image area is the entire radiation image. That is, the number of pixels is 128 in the lateral direction and 154 in the longitudinal direction in the example.

In the threshold value setting unit 41, the initial value of the threshold value used in the binarizing processing of the image data is set. In this example, the first object is to detect the maximum image data (the maximum signal data) of the lung field as the subject field, and the second object is to detect the minimum image data (the minimum signal value) in a mediastinum and abdominal field. In order to accomplish these objects, it is necessary to change the threshold value for binarizing gradually from a larger value to the optimum threshold value, and at the same time, to change the aforementioned threshold value gradually from a smaller value to the optimum threshold value.

At first, in order to find the maximum image data in the lung field, the maximum value M2 of the image data apart from the low density portions of 50, 60, 70, and 80 lines in the almost central portion of the aforementioned effective image area is found, and then the initial value P2 is set by adding 100 to the maximum value M2.

The binarizing/labeling processing is conducted in the same manner as the example of the aforementioned chest side view. In this example, since image noise has been removed by filter processing, labeling is conducted on image data which has two or more pixels in succession.

The image area judgement unit 44 judges whether the desired image area exists or not in a plurality of image areas determined as above. That is, the image area judgement unit 44 judges whether the image area is the desired image area or not according to the relative positional relation of the aforementioned plurality of image areas in the effective image area, and when there are at least one or more image areas, the process advances to the next image data extraction unit. When there is not the desired image area, the threshold value is decreased, and processing from binarizing is repeated.

Figure 12:
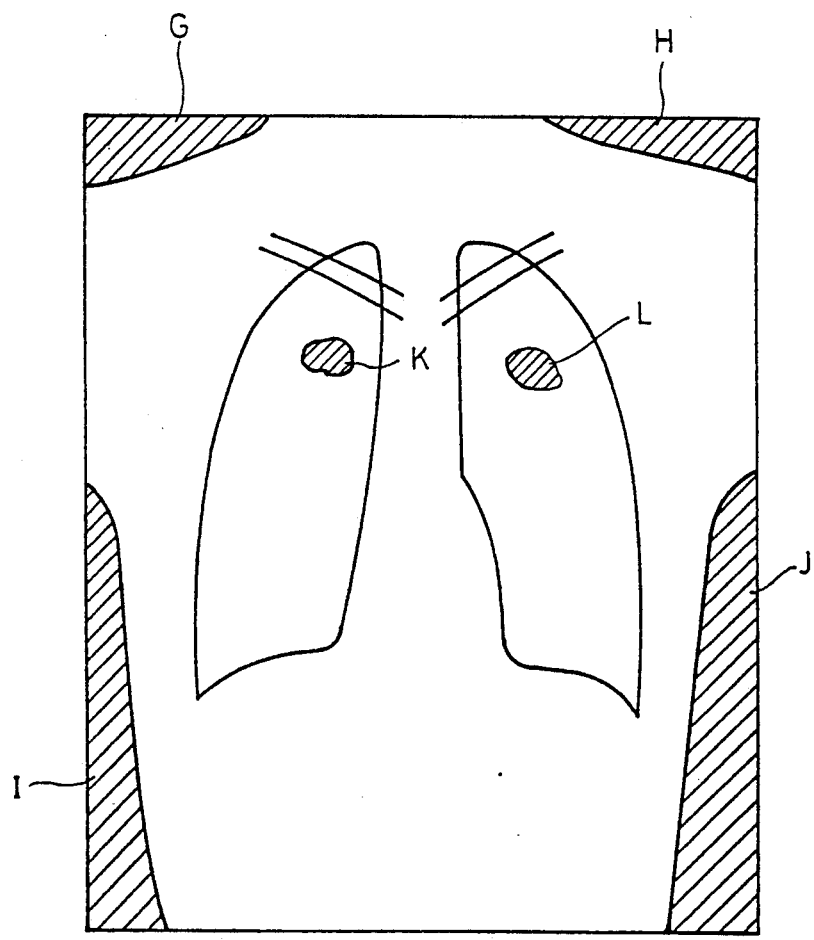

In this example, when 6 areas of G, H, I, J, K and L are labeled as shown in FIG. 12, the areas of G, H, I and K which contact with any one of the upper, lower, left or right end portions of the aforementioned labeled areas, are rejected, and the areas of K and L are determined as the desired image areas.

In an image data extraction unit 45, the image data in the aforementioned B and C areas is statistically processed, and then the maximum value of the image data in the desired area is extracted. The maximum value expresses almost maximum image data (the maximum signal value) S2 in the lung field as the subject field. The average value, minimum value, intermediate value, histogram processing and the like, except the maximum value, may be used as the aforementioned statistical processing, the same as the case of the chest side view.

Next, the minimum value M3 of the entire image data in the aforementioned effective image area is found as the initial value P3 of the threshold value in order to find the minimum image data in the mediastinum and abdominal field, and the initial value P3 is set by subtracting 100 from the minimum value M3. The reason is as follows: the image data in the mediastinum and abdominal field in the subject has the minimum value in the front view of the chest.

In the binarizing unit 42 and the labeling unit 43, the binarizing/labeling processing is conducted in the same manner as the example of the above-mentioned side view of the chest. In this case, since the signal value is small and noise is relatively large in the mediastinum and abdominal field, labeling processing is conducted only in the case where four or more pixels are continued.

The image area judgement unit 44 judges whether the desired image area exists or not in a plurality of image areas determined as above. That is, the image area judgement unit 44 judges whether the image area is the desired image area or not according to the relative positional relation of the aforementioned plurality of image areas in the effective image area, and when there are at least one or more image areas, the process advances to the next image data extraction unit. When there is not the desired image area, the threshold value is increased, and processing from binarizing is repeated.

Figure 13:
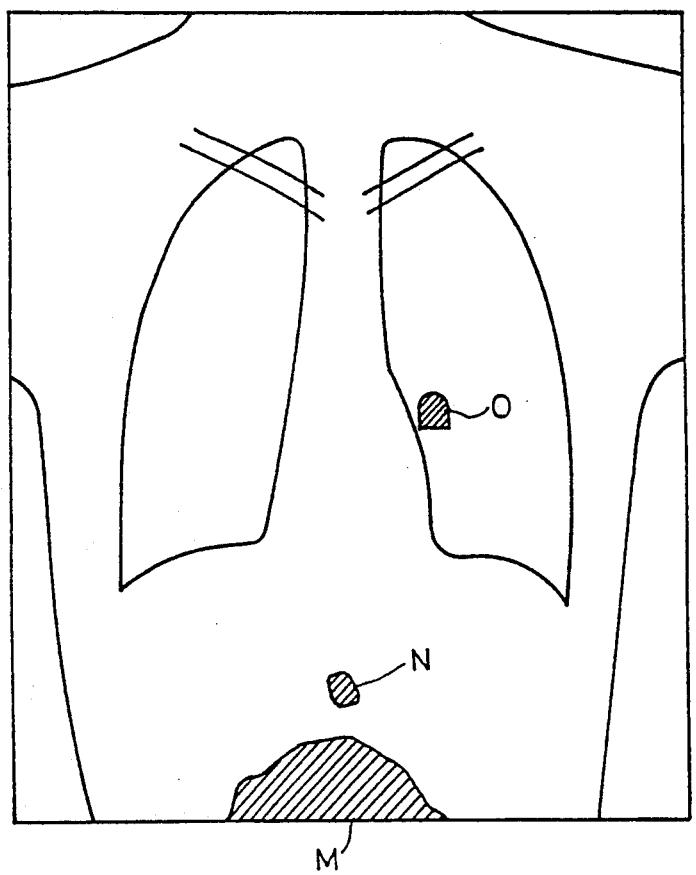

In the example, when three areas of M, N and O are labeled as shown in FIG. 13, the area K which comes into contact with the lower end portion of the effective image area in the aforementioned labeled areas, is determined as the desired image area, and the areas of N and O which do not come into contact with the lower end portion, are rejected. The reason is as follows: in the front view of the chest, there is an area in which the image data has the minimum value near the lower edge of the effective image area; and when the labeled area is not in the near portion of the lower edge, there is a high possibility that it is an image of an artificial structural component such as a pace-maker.

In the image data extraction unit 45, image data in the aforementioned area M is processed into the form of an accumulative histogram, and then 20% of image data are extracted from the smaller desired image area. This value expresses almost minimum image data (the minimum signal value) S3 in the mediastinum and abdominal field as the subject field. The maximum value, minimum value, intermediate value, and average value processings, except the histogram processing, can be used as the aforementioned statistical processing, the same as in the case of the side view of the chest.

Figure 14:
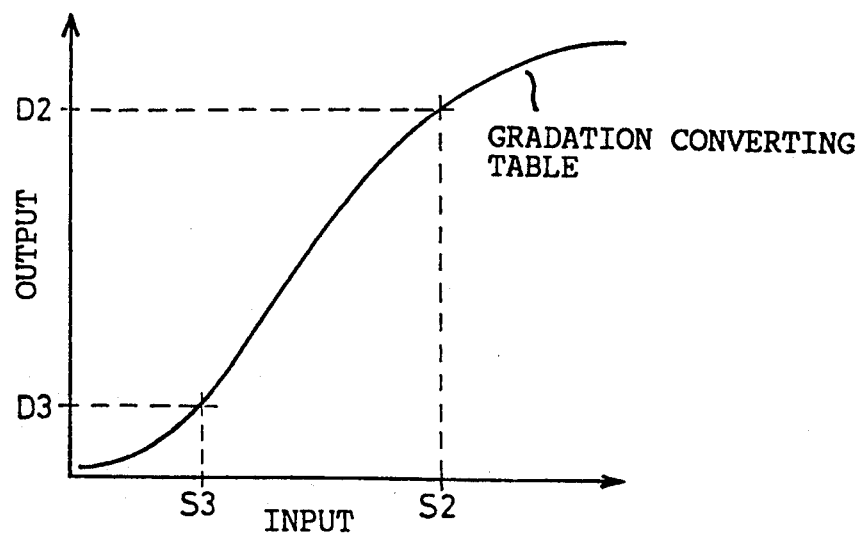
FIG. 14 is a diagram indicating the gradation conversion table.

When almost maximum image data S2 in the lung field and almost minimum image data S3 in the mediastinum and abdominal field are extracted from each image, a gradation processing condition determination unit 46 determines the gradation processing condition according to the maximum image data in the aforementioned lung field and the almost minimum image data in the mediastinum and abdominal field. The gradation processing condition is determined as follows: for example, as shown in FIG. 14, a gradation conversion table is set in which the pixel corresponding to the maximum image data S2 in the lung field and the pixel corresponding to the minimum image data S3 in the mediastinum and abdominal field have density D2 and D3 which can be easily read in a diagnosis (for example, a penetration density 2.0 in the lung field, 0.3 in the mediastinum and abdominal field). A gradation processing unit 47 gradation-processes the entire original radiation image data according to the gradation processing condition determined in the manner described above.

As described above, image data from the lung field to the mediastinum and abdominal field as the subject field can be assigned to a preferable density range in the diagnosis for each image without being influenced by photographing conditions or physical constitution, and thereby appropriate image processing can be stably conducted and diagnostic property can be improved.

In setting of the aforementioned gradation conversion table, as disclosed in Japanese Patent Publication Open to Public Inspection No. 83149/1984, rotation and parallel displacement on the coordinate of a basic gradation conversion table may be used for the aforementioned gradation processing.

Further, in the aforementioned example, image processing has been explained by the use of gradation processing, as an example. However, besides the gradation processing, space-frequency processing as disclosed in, for example, Japanese Patent Examined Publication No. 62376/1987 may be set according to the extracted image data as described above.

Furthermore, radiation image data on which gradation processing is conducted according to the present invention, may be visualized at once by the image output apparatus 15, and further, the image data may be stored once in an image filing system, and then read out therefrom to be outputted to a film, or may be displayed on a CRT.

When the radiation image is stored in the filing system, the radiation image data on which the gradation processing according to the present invention has been conducted, may be stored. Further, original radiation image data which has not yet been processed, and the gradation processing condition (gradation conversion table), determined according to the present invention, may be stored in combination with each other, and when data is read out, gradation processing may be conducted on the data.

Furthermore, the example is structured in a manner in which a stimulative fluorescent substance is used as an X-ray detector, and image data read out photoelectrically from the detector is gradation-processed. However, the present invention is not limited to the system in which the stimulative fluorescent substance is used. The present invention may be structured in a manner in which: other kinds of radiation detectors are used; or a radiographic image which is recorded on a silver-salt film is photoelectrically read out and gradation-processed.

In the aforementioned example, the chest portion of a human body has been taken as an example. However, bones of a leg may be mainly photographed, or a flesh of an abdomin may be mainly photographed. The subject is not limited to the example.

As described above, a desired image area is determined according to image data in the present example, and therefore, an image area to determine an image processing condition is extracted from a radiographic image and thereby the optimum data for image processing can be secured without being influenced by the body form of the patient, photographic conditions, positioning in photographing, or the like. Especially, when a radiographic image is divided into a plurality of image areas according to the image data, and after that, a desired image area is determined from those image areas, the present invention is very effective for image processing.

Furthermore, in the present invention, since a desired image area is determined according to image data, the optimum image processing condition can be set according to the image data in the desired image area without being influenced by the body form of a patient, photographing condition, positioning of photographing or the like, and thereby a subject area can be reproduced which is easily readable and stably finished, resulting in an improvement of diagnostic property.

Furthermore, according to the present invention, an algorithm to determine the desired image area can be simple, processing speed can be improved, and an image processing apparatus can be simplified.

What is claimed is:

1. An apparatus for processing digital image data of pixels which are obtained by radiographing an image area including a subject so as to generate image signals, said image signals being converted into digital image data of pixels, each said digital image data of pixels representing a density level corresponding to an amount of radioactive rays transmitted through a respective portion of said radiographed image area, and each pixel having a position data representing the position of the respective pixel on said image area, said apparatus comprising:

means for determining a threshold value on the basis of digital image data of said subject;
   means for binarizing each said digital image data of pixels of said image area by comparison with said threshold value so that each pixels is represented by a binary code;
   means for classifying each pixel in accordance with its binary code and its position data, and for dividing said image area into plural sub-image areas so that all pixels adjoining each other in the same sub-image area have the same binary code;
   means for comparing said digital image data and the position data of each of said plural sub-image areas with a predetermined condition to produce a comparison result, and for selecting a desired sub-image area from said plural sub-image areas responsive to the comparison result; and
   means for determining an image processing condition for said digital image data of said image area on the basis of said digital image data of said desired sub-image area.

2. The apparatus of claim 1, wherein said threshold value-determining means comprises means for determining said threshold value on the basis of picked-up digital image data in a predetermined area at a center portion of said image area.

3. The apparatus of claim 2, wherein said picked-up digital image data indicates a maximum density level in said predetermined area.

4. The apparatus of claim 2, wherein said picked-up digital image indicates a minimum density level in said predetermined area.

5. The apparatus of claim 1, wherein said threshold value-determining means includes means for producing a histogram of said digital image data and for determining said threshold value on the basis of a value in a portion of said histogram corresponding to the subject.

6. The apparatus of claim 5, wherein said value on the basis of which said threshold value-determining means determines said threshold value indicates the maximum density level in said portion of said histogram corresponding to the subject.

7. The apparatus of claim 5, wherein said value on the basis of which said threshold value-determining means determines said threshold value indicates the minimum density level in said portion of said histogram corresponding to the subject.

8. The apparatus of claim 1, wherein said threshold value-determining means includes means for picking up said digital image data along a line across said image area and for determining said threshold value on the basis of a value in a portion corresponding to the subject on said line.

9. The apparatus of claim 8, wherein said value on the basis of which said value-determining means determines said threshold value indicates the maximum density level in said portion corresponding to the subject on said line.

10. The apparatus of claim 8, wherein said value on the basis of which said value-determining means determines said threshold value indicates the minimum density level in said portion corresponding to the subject on said line.

11. The apparatus of claim 1, wherein, when said selecting means does not select said desired sub-image area in consideration of the comparison result, said threshold value-determining means changes said threshold value to another threshold value and said binarizing means binarizes each of said digital image data of pixels with said another threshold value.

12. The apparatus of claim 1, wherein, when said image area includes a non-subject portion, said threshold value is lower than a density level of said non-subject portion of said image area.

13. The apparatus of claim 1, wherein said threshold value is higher than a density level of a high density portion of said image area.

14. A method of processing digital image data of pixels which are obtained by radiographing an image area including a subject so as to generate image signals, said image signals being converted into digital image data of pixels, each said digital image data of pixels representing a density level corresponding to an amount of radioactive rays transmitted through a respective portion of said radiographed image area, and each pixel having a position data representing the position of the respective pixel on said image area, said method comprising:

determining a threshold value on the basis of digital image data of said subject;
   binarizing each said digital image data of pixels of said image area by comparison with said threshold value so that each pixels is represented by one of a binary code;
   classifying each pixel in accordance with its binary code and its position data;
   dividing said image area into plural sub-image areas so that all pixels adjoining each other in the same sub-image area have the same binary code;
   comparing said digital image data and the position data of each of said plural sub-image areas with a predetermined condition, and producing a comparison result;
   selecting a desired sub-image area from said plural sub-image areas responsive to the comparison result; and
   determining an image processing condition for said digital image data of said image area on the basis of said digital image data of said desired sub-image area.

15. The method of claim 14, wherein, when in said step of selecting said desired sub-image area, a desired area cannot be selected, said threshold value is changed to another threshold value and each of said digital image data of pixels is binarized with said another threshold value.

16. The method of claim 14, wherein said image area is divided into a plurality of sub-image areas, each sub-image area having the same binary code.

17. The method of claim 16, wherein said desired image area is selected in accordance with a position of each of the plurality of sub-image areas having the same binary code.

18. The method of claim 14, wherein said subject is a human body.

19. The method of claim 18, wherein said desired image area is a lung field.

* * * * *